United States Patent [19]

Madate et al.

[11] Patent Number: 4,813,778
[45] Date of Patent: Mar. 21, 1989

[54] OPHTHALMIC POSITIONING APPARATUS

[75] Inventors: Haruhisa Madate; Koichi Yano, both of Kawasaki; Isao Matsumura, Yokosuka, all of Japan

[73] Assignee: Canon Kabushiki Kaisha, Tokyo, Japan

[21] Appl. No.: 823,737

[22] Filed: Jan. 29, 1986

[30] Foreign Application Priority Data

Feb. 9, 1985 [JP] Japan .................................. 60-23730

[51] Int. Cl.$^4$ ............................................... A61B 3/14
[52] U.S. Cl. .................................................... 351/208
[58] Field of Search ................. 351/206, 207, 208, 246

[56] References Cited

U.S. PATENT DOCUMENTS 4,257,687 3/1981 Kohayakawa ..................... 351/208
4,511,227 4/1985 Nunokawa et al. ................ 351/208

FOREIGN PATENT DOCUMENTS 84145A 6/1980 Japan .

*Primary Examiner*—Rodney B. Bovernick
*Attorney, Agent, or Firm*—Fitzpatrick, Cella, Harper & Scinto

[57] ABSTRACT

An ophthalmic positioning apparatus has: an optical index projection system for projecting a positioning index onto the cornea of an eye to be examined; and optical focusing system for forming a cornea-reflected image of the positioning index on a predetermined focusing plane; an observing device for observing the cornea-reflected image of the positioning index which is formed on the predetermined focusing plane; and a moving device for moving the optical index projection system, the optical focusing system, and the observing device along at least an operation distance adjustment direction; the positioning index being adapted to allow an observer to identify an inverted state of an index image through the observing device when the positioning index is projected onto a surface position of the cornea of an eye and onto a central position of the curvature of the cornea.

1 Claim, 4 Drawing Sheets

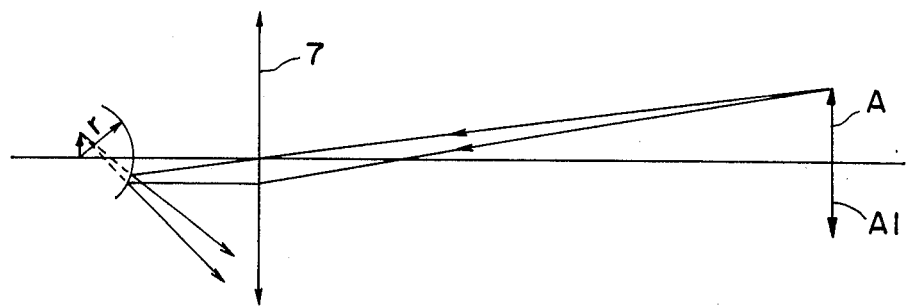
FIG. 4(a)
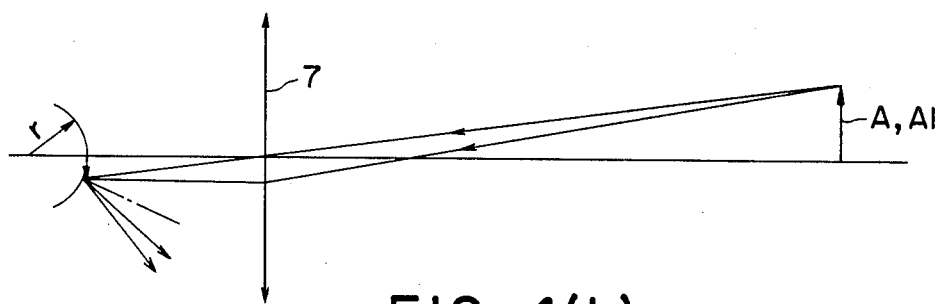
FIG. 4(b)
(a) (b)
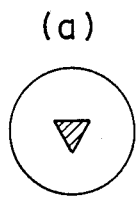 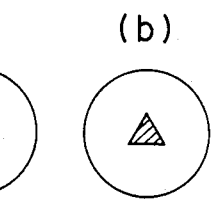
FIG. 5
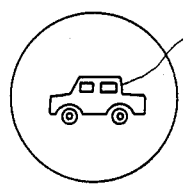
FIG. 6
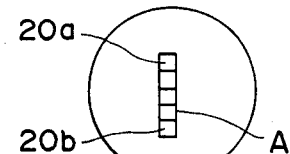
FIG. 7
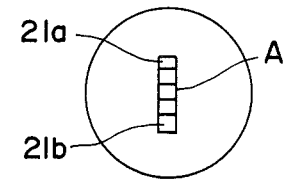
FIG. 8

OPHTHALMIC POSITIONING APPARATUS

BACKGROUND OF THE INVENTION

1. Field of the Invention

The present invention relates to an ophthalmic positioning apparatus which is used in, for example a noncontact type tonometer and which projects a positioning index onto an eye to be examined and performs positioning (alignment control and/or operation distance control) for an ophthalmic instrument with respect to the eye in accordance with an index image reflected by the eye.

2. Description of the Prior Art

In a conventional ophthalmic instrument, exemplified by a noncontact type tonometer using air pulses, air pulses are ejected onto the cornea of an eye to be examined along the axial direction of the instrument. Corneal deformation-sensing light-projecting and light-receiving systems are inclined substantially symmetrically about the axial direction of the ophthalmic instrument. Eye pressure is determined by measuring the time required to cause the light-receiving system to generate a maximum output, that is, the time required to flatten the cornea. However, when the distance between the ophthalmic instrument and the vertex of the cornea does not coincide with a predetermined operation distance or when the vertex of the cornea and the horizontal eye axis do not fall in line with the axis of the ophthalmic instrument, measured values are not accurate. For this reason, a conventional noncontact type tonometer has an optical positioning system to adjust the distance between the tonometer and the vertex of the cornea so that it coincides with the predetermined distance, or to adjust the axis of the tonometer so that it falls in line with the vertex of the cornea. A doctor performs alignment and operation distance adjustment and sends out air pulses so as to clearly form a positioning index image at the center of the field of view in a finder. A noncontact type tonometer with such an optical positioning system is described in U.S. Pat. No. 3,756,073. Although this optical system can perform an operation distance adjustment to clearly focus the cornea-reflected image of the positioning index, two index images of the same size appear at two points with different operation distances and cannot be clearly distinguished from each other. Furthermore, the two points with different operation distances are only slightly separated from each other. In the conventional positioning apparatus, as a result, an index having a position which does not coincide with a normal operation distance can be mistakenly chosen, thus resulting in an inaccurate measurement.

SUMMARY OF THE INVENTION

It is an object of the present invention to provide an ophthalmic positioning apparatus which allows a doctor to easily determine the operation distance error, so that degradation of measurement precision caused by the operation distance error can be prevented.

It is another object of the present invention to provide an automated ophthalmic positioning apparatus wherein positioning can be further simplified.

An aspect of the present invention is an ophthalmic positioning apparatus comprising: an optical index projection system for projecting a positioning index onto the cornea of an eye to be examined; an optical focusing system for forming a cornea-reflected image of the positioning index on a predetermined focusing plane; observing means for observing the cornea reflected-image of the positioning index which is formed on the predetermined focusing plane; and moving means for moving the optical index projection system, the optical focusing system, and the observing means along at least an operation distance adjustment direction. The positioning index is adapted to allow an observer to identify an inverted state of an index image through the observing means when the positioning index is projected onto a surface position of the cornea of the eye and onto a central position of the curvature of the cornea.

BRIEF DESCRIPTION OF THE DRAWINGS

FIGS. 4(a) and 4(b) are schematic views showing optical paths corresponding to FIGS. 3(a) and 3(b), respectively;

FIG. 5 is a front view of an index image according to the present invention;

FIGS. 6 to 8 are front views of indices;

DESCRIPTION OF THE PREFERRED EMBODIMENTS

An embodiment exemplifying a noncontact type tonometer to which the present invention is applied will be described in detail.

Figure 1:
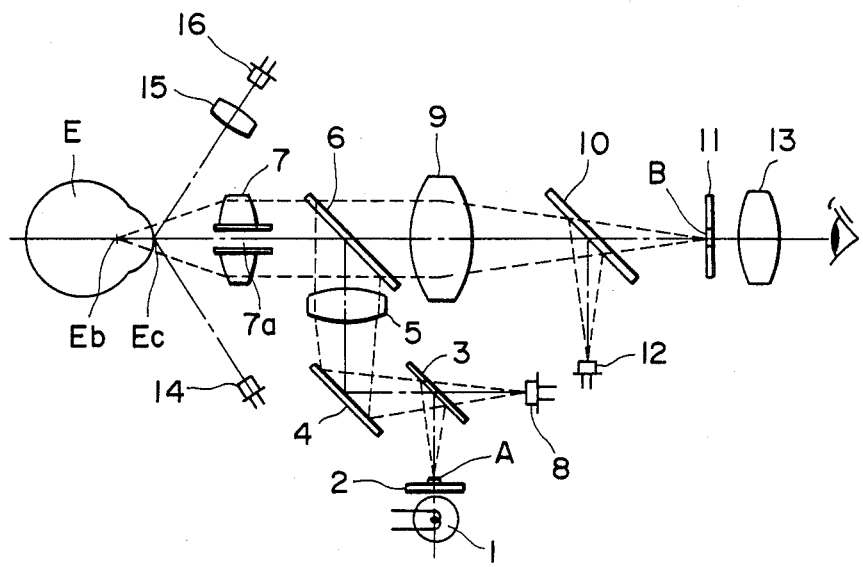
FIG. 1 is a schematic view of an ophthalmic instrument applied to a noncontact type tonometer according to an embodiment of the present invention.

FIG. 1 shows a noncontact type tonometer which, aside from the inclusion of a positioning index, employs the same optical system as that described in U.S. Pat. No. 3,756,073. Referring to FIG. 1, a beam from an illumination lamp 1 is reflected by a half mirror 6 through a positioning index plate 2 obtained by patterning an index A on a light-scattering plate, a dichroic mirror 3 for transmitting infrared rays and reflecting visible light, a total reflection mirror 4 and a lens 5. The reflected beam propagates to the left and is focused by an objective lens 7 with an air pulse emission orifice 7a at its center. The focused beam is incident on a center Eb of curvature of the cornea of an eye E to be examined. An infrared diode 8 is arranged behind the dichroic mirror 3 and located at a conjugate position with the index plate 2.

An index image directed toward the center Eb of curvature of the cornea is reflected by a cornea Ec and is collimated by the objective lens 7. The parallel beam passes through the half mirror 6, a lens 9, and a dichroic mirror 10 for reflecting infrared rays and transmitting visible light. The transmitted beam is focused on a transparent plate 11, on which a reference circle B is drawn. The infrared light is reflected by the dichroic mirror 10 and is focused on an infrared detection diode 12 located at a conjugate position with the reference circle B. A doctor can adjust a visible light index image located within the reference circle B through an eyepiece 13 of a finder along a direction (i.e., alignment direction)

perpendicular to the optical axis and along the direction (i.e., operation distance direction) of the optical axis by moving the tonometer itself. An infrared diode 14 emits parallel light which is projected on the cornea Ec in an inclined direction. When the vertex portion of the cornea Ec is changed from a projection to a flat surface, i.e., when the cornea Ec is flattened by air pulses, the beam from the infrared diode 14 is most sharply focused on the infrared detection diode 16 through the lens 15.

When the doctor completes positioning and depresses a measurement button, a positioning detector starts to emit air pulses from the orifice 7a at the center of the objective lens 7 to the vertex Ea of the cornea. In this case, the pressure and the time of air pulses have a predetermined relationship. When the vertex portion of the cornea Ec is flattened by the air pulses, the parallel beam from the infrared diode 14 is most effectively focused on the infrared detection diode 16 through the lens 15. The time required to flatten the vertex portion of the cornea Ec is measured to calculate eye pressure.

If the doctor depresses the measurement button when the image of the index A is not accurately located within the reference circle B, no air pulses are emitted. The eye pressure measuring circuit is operated only when an output is generated from the infrared detection diode 12. The infrared.. diode 8 and the infrared detection diode 12 thus serve as a safety mechanism for preventing measurement in an incomplete alignment state.

As described above, when positioning is performed using a conventional circular index, identical index images are observed at two positions with different operation distances due to reflection by the cornea Ec.

Figure 2:
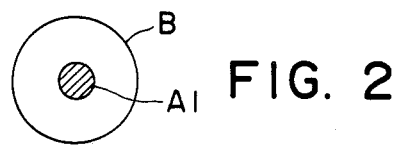
FIG. 2 is a front view of a conventional index image.
Figure 3:
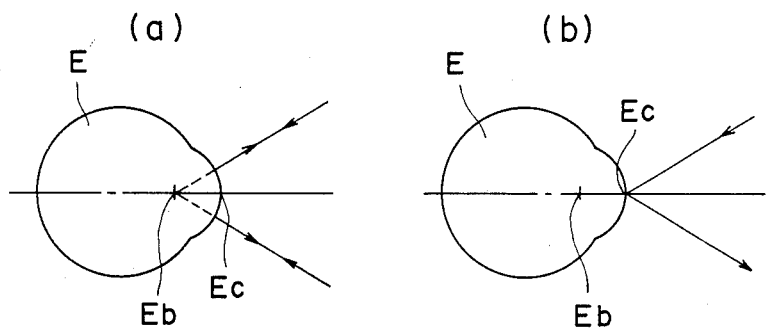
FIGS. 3(a) and 3(b) are schematic views for explaining the positioning operation.

FIG. 2 shows an index image A1 observed by the doctor when the conventional index is used. The index image A1 is observed within the reference circle B. If the index image A1 is inverted long the vertical and horizontal directions, it cannot be identified. Upon consideration of the reason why identical index images are observed at two points with different operation distances, the following conclusion is derived. As shown in FIG. 3(a), when the index image is focused toward the center Eb of curvature of the eye E, the beam reflected by the surface of the cornea is emitted from an object located at a position as the center Eb of curvature of the cornea Ec and is focused by the objective lens 7 and the like onto the reference circle B. As shown in FIG. 3(b), however, when the operation distance is increased by the radius of curvature of the cornea, the index image is focused at the vertex of the cornea Ec and is reflected. The reflected beam is focused on the reference circle B in the same manner as in FIG. 3(a). In the reflection states in FIGS. 3(a) and 3(b), the index image (FIG. 3(b)) on the reference circle B is observed to be normally rotated, while the index image (FIG. 3(a)) on the reference circle B is observed to be inverted in the vertical and horizontal directions. However, when the index A is circular, inversion cannot provide a sufficient basis for identification. Furthermore, since an increase in operation distance is as small as the radius of curvature of the cornea, e.g., about 7 mm, it is difficult to identify the real index image.

According to an embodiment of the present invention, the shape, color and brightness of the upper and left portions of the index A on the positioning index plate 2 in FIG. 1 are asymmetrical with those of the lower and right portions. Even if the index A is rotated through 180°, the index image can be easily identified. For example, if the index A on the positioning index plate 2 has a triangular shape and the index image A1 is vertically inverted within the reference circle B, the index image can be identified by visually checking whether the vertex of the triangle is located at the upper or lower position, as shown in FIG. 5(b) or 5(a).

As shown in FIG. 6, if the index A is represented by a normal object such as a motor vehicle, the normal state can be easily discriminated from the inverted state. Furthermore, as shown in FIG. 7, the index A is constituted by an array of phosphors such that an upper light emitting member 20a has the highest light intensity and a lower light emitting member 20b has the lowest light intensity. In this case, inversion of the index A can be easily identified. Alternatively, as shown in FIG. 8, the index A can be constituted by an array of color markers such that upper and lower portions 21a and 21b have different colors.

Figure 9:
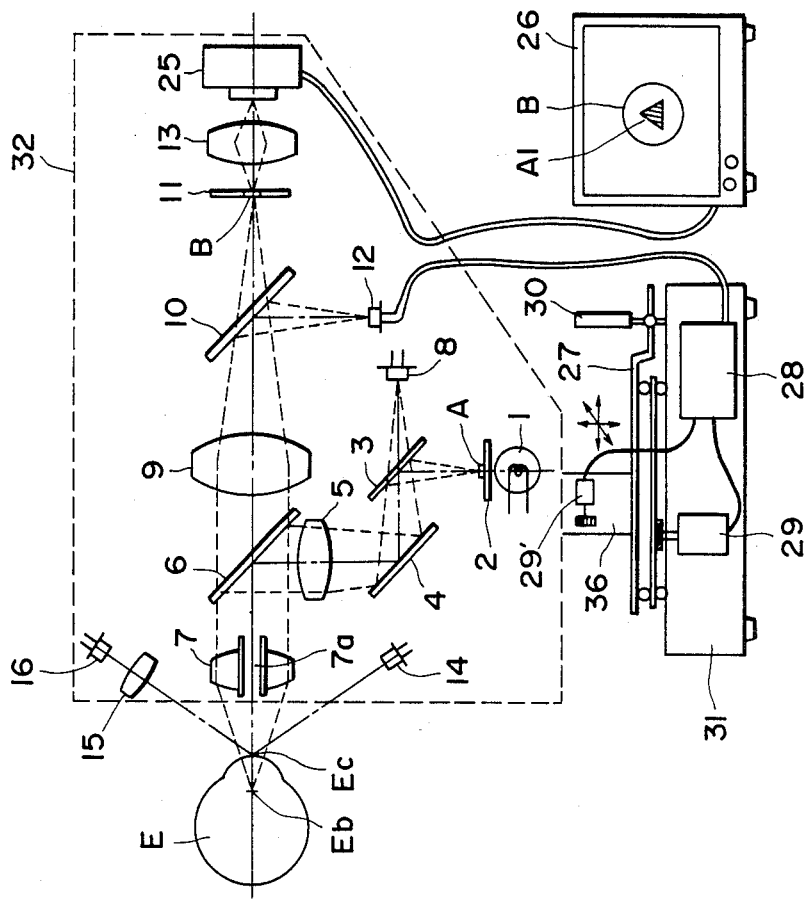
FIG. 9 is a schematic view showing an automatic positioning apparatus according to another embodiment of the present invention.

FIG. 9 shows an automatic positioning apparatus according to another embodiment of the present invention. The apparatus has a television camera 25 and a monitor 26 to allow a doctor to observe the index image on the monitor 26.

Referring to FIG. 9, an X-Y stage 27 is moved by a motor 29 on a horizontal plane such that an output from the infrared detection diode 12 exceeds a predetermined value. The motor 29 is controlled by a control circuit 28. A column 36 is vertically moved by a motor 29'. A joystick 30 is mounted on a base 31. When the operator or doctor selectively moves the joystick 30 in four directions, a housing 32 can be moved manually within the horizontal plane. In addition, when the joystick 30 is rotated, the housing 32 is vertically moved through a mechanism (not shown). When the apparatus is misaligned with the eye to be examined, the output from the infrared detection diode 12 is small. Therefore, the X-Y stage 27 is moved automatically to increase the output from the infrared detection diode 12.

Figure 10:
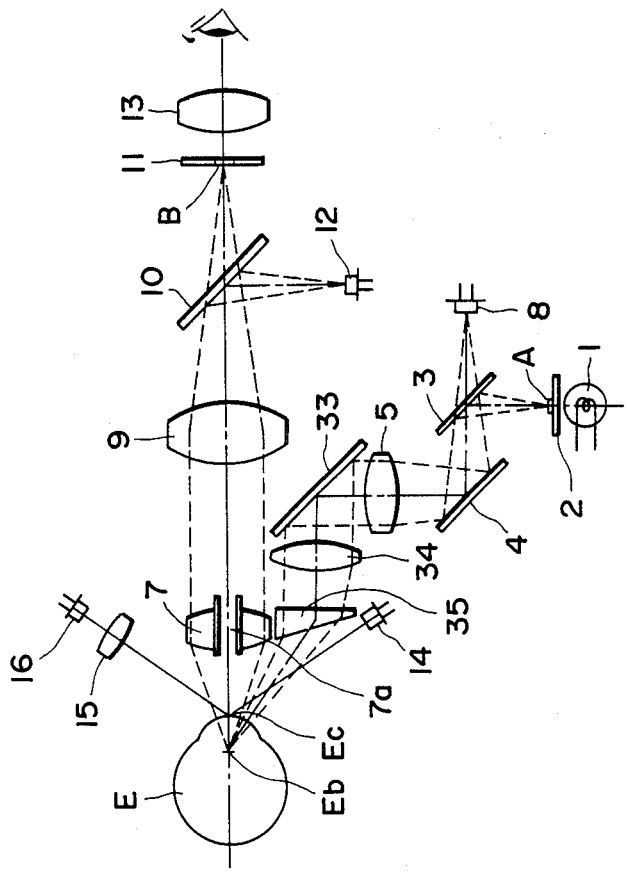
FIG. 10 is a schematic view showing a modification for projecting a positioning index onto an eye through an objective lens.

When the operation distance between the apparatus and the eye to be examined is in error, an output from the infrared detection diode 12 is small. In order to increase this output, the doctor observes the image state of the positioning index 2 on the monitor 26. Alternatively, automatic operation distance control can be made utilizing the output from the infrared detection diode 12. FIG. 10 shows a modification of the embodiment in FIG. 1. The positioning index A is projected onto the eye to be examined without passing through the objective lens 7. The positioning index A is projected near the cornea of the eye through the dichroic mirror 3, the total reflection mirror 4, the lens 5, a total reflection mirror 33, a lens 34 and a wedge prism 35.

What is claimed is:

1. A positioning method for positioning an ophthalmic apparatus with respect to an eye to be examined in the direction of the eye optical axis, comprising the steps of:

projecting an asymmetrical-shaped positioning index provided in the ophthalmic apparatus onto a cornea of the eye to be examined through an optical index projection system;

moving the ophthalmic apparatus in the direction of the eye optical axis to allow observation of a blur image of a cornea-reflected image of said asymmetrical positioning index through an imaging optical system;

moving the ophthalmic apparatus in the direction of the eye optical axis to allow observation of an erect image of the cornea-reflected image of said asymmetrical positioning index through said imaging optical system;

moving the ophthalmic apparatus in the direction of the eye optical axis to allow observation of an inverted image of the cornea-reflected image of said asymmetrical positioning index through said imaging optical system;

stopping the ophthalmic apparatus when said inverted image of the cornea-reflected image of said asymmetrical positioning index is observed.

* * * * *